United States Patent
Howard, III et al.

(10) Patent No.: US 6,197,003 B1
(45) Date of Patent: Mar. 6, 2001

(54) CATHETER ADVANCING SINGLE-HANDED SOFT PASSER

(75) Inventors: Matthew A. Howard, III, Iowa City; Charles Garrell, Coralville; Patrick Hitchon, Iowa City, all of IA (US); Christopher Loftus, Oklahoma City, OK (US)

(73) Assignee: University of Iowa Research Foundation, Iowa City, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/911,907

(22) Filed: Aug. 15, 1997

(51) Int. Cl.[7] ..................................................... A61M 5/178
(52) U.S. Cl. .............................. 604/164.12; 604/164.01
(58) Field of Search .................. 604/27, 49, 51, 604/54, 93, 117, 164, 165, 170, 198, 227, 264, 272, 280, 283, 164.01–164.13; 606/108

(56) References Cited

U.S. PATENT DOCUMENTS

| | | | |
|---|---|---|---|
| 1,654,905 | * 1/1928 | Voos ...................................... | 604/164 |
| 2,740,404 | * 4/1956 | Kohl ...................................... | 604/198 |
| 2,923,295 | * 2/1960 | Guerriero .............................. | 604/164 |
| 3,118,447 | * 1/1964 | Hunt et al. ............................. | 604/164 |
| 3,356,089 | * 12/1967 | Francis .................................. | 604/164 |
| 3,906,946 | * 9/1975 | Nordstrom ............................ | 604/164 |
| 4,353,369 | * 10/1982 | Muetterties et al. .................. | 604/272 |
| 4,613,324 | 9/1986 | Ghajar ..................................... | 604/49 |
| 4,713,049 | * 12/1987 | Carter ....................................... | 604/8 |
| 4,762,516 | * 8/1988 | Luther et al. .......................... | 604/164 |
| 4,889,188 | * 12/1989 | Schwiegerling ...................... | 604/164 |
| 4,998,938 | 3/1991 | Ghajar et al. .......................... | 606/130 |
| 5,176,651 | * 1/1993 | Allgood et al. ....................... | 604/164 |
| 5,569,267 | 10/1996 | Howard et al. ....................... | 606/130 |
| 5,762,630 | * 6/1998 | Bley et al. ............................. | 604/164 |
| 5,807,339 | * 9/1998 | Bostrom et al. ...................... | 604/164 |
| 5,823,961 | * 10/1998 | Fields et al. .......................... | 600/434 |

* cited by examiner

*Primary Examiner*—Sharon Kennedy
(74) *Attorney, Agent, or Firm*—Fleshner & Kim, LLP

(57) ABSTRACT

Catheter advancing assembly having a stylet including a shaft, and a catheter advancing piece including a rod having a bore therethrough. The bore of the rod accommodates a portion of the shaft of the stylet. A holding unit affixed to the proximal end of the shaft, to be used in conjunction with a grasping unit affixed to the rod, allows for the holding and manipulation of the catheter advancing assembly with only one hand. A method for making a catheter advancing assembly of the invention is disclosed, as well as a method for advancing a ventricular catheter within a ventricular catheter in a "soft" manner using only one hand.

21 Claims, 7 Drawing Sheets

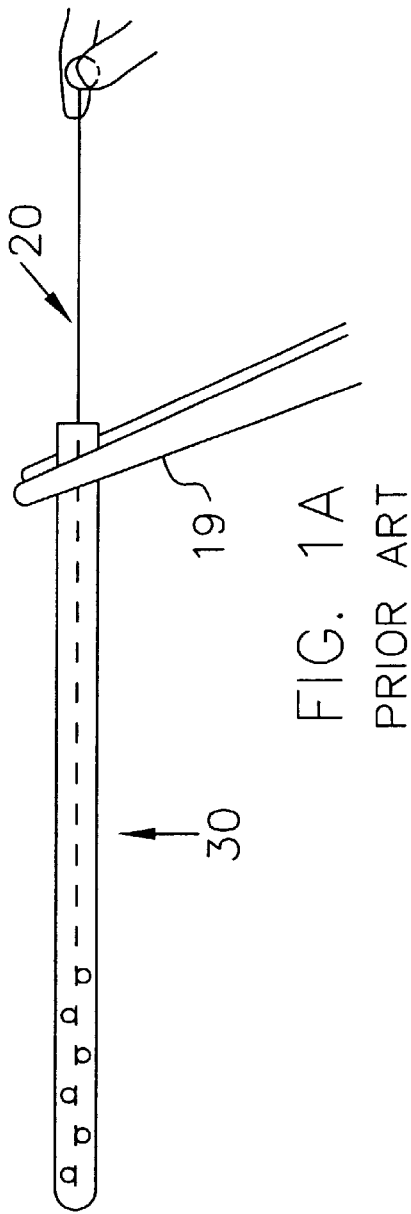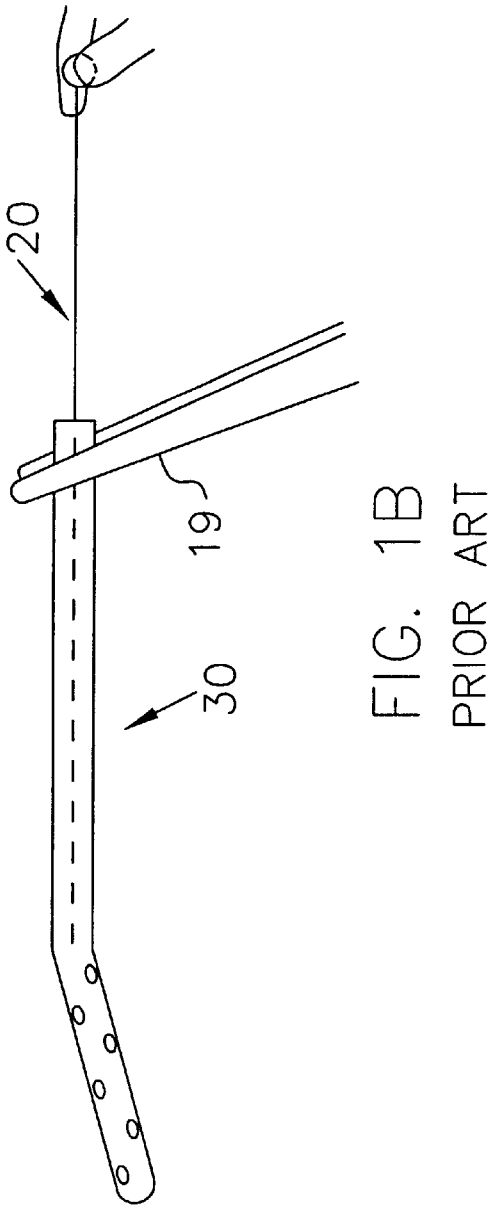
FIG. 1A PRIOR ART
FIG. 1B PRIOR ART

CATHETER ADVANCING SINGLE-HANDED SOFT PASSER

BACKGROUND OF THE INVENTION

1. Field of the Invention

This invention relates to a catheter advancing assembly and method for advancing a catheter within a patient. In particular, this invention relates to a catheter advancing assembly for soft passing a catheter within a patient, wherein the catheter advancing assembly is manipulated with a single hand. More particularly, this invention relates to a single-handed catheter advancing assembly and method for soft passing a catheter within the lateral cerebral ventricles of a patient. This invention further relates to a method of making a single-handed catheter advancing assembly.

2. Background of the Related Art

Ventriculoperitoneal (VP) shunt placement for hydrocephalus is one of the most common procedures in neurological surgery. Hydrocephalus may result from subarachnoid hemorrhage, trauma, tumors, and the like. The technique entails introducing a catheter through brain tissue into one of the lateral ventricles of the brain. Cerebrospinal fluid in the ventricle may be vented through the catheter to relieve signs, symptoms, and sequelae of hydrocephalus.

The current surgical technique for placement of VP shunts was developed in the 1950's and has persisted with few modifications prior to the invention. Despite the relative simplicity of this procedure, the complication rate can be significant and includes operative morbidity as well as post-operative infections and obstructions, etc. Surgical technique plays a major role in reducing complications associated with VP shunts. Improper placement of the ventricular catheter may result in neurologic injury from the misplaced catheter or may cause an early proximal shunt obstruction, which is often secondary to blockage by adherent choroid plexus and other debris. The incidence of misplaced catheters is variable and dependent on a variety of factors, including the experience of the surgeon, the size of the targeted ventricle, the surgical approach, and the use of intraoperative guidance, such as fluoroscopy, ultrasound, or endoscopy. Thus, to optimize shunt function and minimize morbidity, proper placement of the catheter is essential. In this regard, a simple mechanical device, known as the Caroline Guide, which prevents insertion of a ventricular catheter along an incorrect trajectory, is taught by Howard III, et al. in U.S. Pat. No. 5,569,267, the contents of which are incorporated herein by reference in their entirety.

The trajectory or path of the catheter in ventricular catheter placement can be considered in two parts: firstly, passage through brain tissue for the catheter tip to gain access to the ventricular cavity; and secondly, advancing the catheter tip further into the fluid-containing cavity. Many surgeons prefer to "soft pass" the distal end of the catheter during the second part of the trajectory, i.e the stylet is removed from the distal end of the catheter as the catheter tip is advanced within the ventricular cavity.

With conventional apparatus and methods for soft passing a ventricular catheter, the surgeon uses one hand to advance the catheter while the other hand is used to hold the end of the stylet. The instant invention provides a catheter advancing assembly, and method, which allows the surgeon to soft pass a ventricular catheter using only one hand, as will be described fully hereinbelow.

The above references are incorporated by reference herein where appropriate for appropriate teachings of additional or alternative details, features and/or technical background.

SUMMARY OF THE INVENTION

An object, therefore, of the invention is to provide a catheter advancing assembly for single-handed soft passing the distal end of a ventricular catheter within a cerebral ventricle.

Another object of the invention is to provide a catheter advancing assembly which can be readily grasped and manipulated with one hand.

Another object of the invention is to provide a catheter advancing assembly including first and second finger pieces for accommodating an index finger and a middle finger, respectively, and a thumb piece for accommodating a thumb of an operator of the catheter advancing assembly.

Another object of the invention is to provide a method for making a catheter advancing assembly which includes first and second finger pieces for accommodating an index finger and a middle finger, respectively, and a thumb piece for accommodating a thumb, wherein the catheter advancing assembly can be readily grasped and manipulated with one hand.

Another object of the invention is to provide a method for advancing a ventricular catheter within a cerebral ventricle using only one hand, wherein the distal end of the catheter is advanced in a "soft" manner.

Another object of the invention is to provide a method for single-handed soft passing a ventricular catheter within a cerebral ventricle of a patient.

One advantage of the invention is that it provides a catheter advancing assembly which allows soft passing of a catheter within a cerebral ventricle, wherein the catheter advancing assembly can be readily grasped and manipulated using only one hand.

Another advantage of the invention is that it provides a catheter advancing assembly including first and second finger pieces for accommodating the index finger and middle finger, respectively, of an operator of the catheter advancing assembly, wherein a ventricular catheter can be soft passed within the cerebral ventricle by extending the index and middle fingers away from the thumb of the operator of the catheter advancing assembly.

Another advantage of the invention is that it provides a method of soft passing a ventricular catheter within the cerebral ventricle by extending the index and middle fingers away from the thumb of the operator of the catheter advancing assembly.

One feature of the invention is that it provides a catheter advancing assembly which includes a stylet having a shaft and a thumb piece, in combination with a catheter advancing piece including a grasping unit and a rod having a bore therethrough.

Another feature of the invention is that it provides a catheter advancing assembly featuring single-handed manipulation and operation thereof.

Another feature of the invention is that it provides a catheter advancing piece including a rod, the rod having first and second finger pieces affixed, preferably bilaterally, thereto.

Another feature of the invention is that it provides a method for single-handed soft passing of a ventricular catheter.

These and other objects, advantages and features are accomplished by the provision of a catheter advancing assembly for single-handed soft passing a ventricular catheter, wherein the assembly includes: a stylet including a shaft and a holding unit; and, a catheter advancing piece including a rod and a grasping unit, the rod having a bore therethrough, the bore capable of housing at least a portion of the shaft, and the shaft capable of moving longitudinally within the bore.

These and other objects, advantages and features are accomplished by the provision of a catheter advancing assembly for single-handed soft passing a ventricular catheter, the assembly including: a stylet having a shaft and a holding unit; and, a catheter advancing piece, wherein the catheter advancing piece includes a first finger piece and a second finger piece, and a rod having a distal end and a proximal end, wherein the first finger piece and the second finger piece are arranged, preferably, bilaterally, on the rod towards the proximal end of the rod.

These and other objects, advantages and features are accomplished by the provision of a catheter advancing assembly for single-handed soft passing a ventricular catheter, wherein the assembly includes: a catheter advancing cylinder including a rod, a first finger piece, and a second finger piece, the rod having a bore therethrough; and, a stylet including a thumb piece and a shaft, the shaft having a distal end and a proximal end, and the thumb piece affixed at the proximal end of the shaft, the shaft having a length greater than the length of the rod, and the shaft capable of longitudinal movement within the bore.

These and other objects, advantages and features are accomplished by the provision of a catheter advancing assembly, including: a stylet including a shaft, the shaft having a proximal end, and the stylet further including a thumb piece, the thumb piece affixed to the proximal end of the shaft; and a catheter advancing piece including a rod and a grasping unit, the grasping unit affixed to the rod, the rod having a bore therethrough, the bore capable of housing the proximal end of the shaft, the shaft having a diameter slightly less than the diameter of the bore.

These and other objects, advantages and features are accomplished by the provision of a method for making a catheter advancing assembly, the method including the steps in any order of: a) providing a shaft of a stylet, the shaft having a proximal end; b) affixing a thumb piece to the proximal end of the shaft; c) providing a rod of a catheter advancing cylinder, the rod having a bore therethrough, the bore for housing at least a portion of the shaft, and the bore having a diameter substantially the same as the diameter of the shaft; and d) affixing a first finger piece and a second finger piece to the rod.

These and other objects, advantages and features are accomplished by the provision of a method for making a catheter advancing assembly, including the steps in any order of: a) providing a shaft of a stylet, the shaft having a proximal end; b) affixing a holding unit to the proximal end of the shaft; c) providing a rod of a catheter advancing cylinder, the rod having a bore therethrough, the bore for housing a portion of the shaft, and the bore having a diameter slightly less than the diameter of the shaft; d) affixing a grasping unit to the rod.

These and other objects, advantages and features are accomplished by the provision of a method for single-handed soft passing a ventricular catheter within a cerebral ventricle of a patient, including the steps in any order of: a) coupling a catheter advancing piece to a shaft of a stylet, the shaft having a proximal end and a distal end, wherein the proximal end of the shaft is housed within a bore of the catheter advancing piece; b) coupling a ventricular catheter to the distal end of the shaft, the ventricular catheter having a channel therein, wherein the distal end of the shaft is housed within the channel; c) advancing the ventricular catheter, the catheter advancing piece, and the stylet, as a unit, towards a cerebral ventricle until the distal end of the ventricular catheter has penetrated the cerebral ventricle; and d) advancing the ventricular catheter and the catheter advancing piece preferably, as a unit, such that the distal end of the ventricular catheter is soft passed within the cerebral ventricle.

These and other objects, advantages and features will become more apparent from the following description of embodiments thereof taken in conjunction with the accompanying drawings.

Additional advantages, objects, and features of the invention will be set forth in part in the description which follows and in part will become apparent to those having ordinary skill in the art upon the disclosure of the invention herein. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 1A and FIG. 1B represent soft pass catheter advancement of the prior art using conventional equipment;

DETAILED DESCRIPTION OF PREFERRED EMBODIMENTS

Figure 2A:
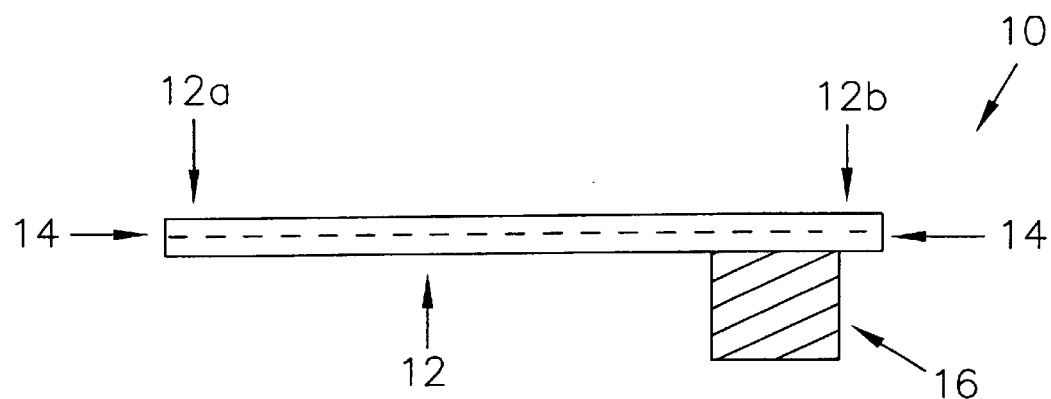
FIG. 2A shows a catheter advancing piece according to one embodiment of the invention.

The instant invention provides a catheter advancing assembly which is unique in its design and operation, and which can be used by a surgeon for soft passing a ventricular catheter into a cerebral ventricle using only one hand.

Referring now to the drawings, FIG. 1A shows ventricular catheter advancement according to the prior art using conventional equipment, in which a stylet 20 extends almost the entire length of the catheter 30, thereby providing an element of rigidity to catheter 30 including its distal end. Using the conventional method and equipment of FIG. 1A, two hands are required to advance catheter 30: the surgeon uses one hand to secure (and move) stylet 20, while the proximal end of catheter 30 is manipulated by forceps 19 held in the surgeon's other hand. FIG. 1B shows ventricular catheter advancement in a "soft" manner, according to the prior art using conventional equipment, in which stylet 20 does not occupy the distal portion of catheter 30 thereby decreasing the degree of rigidity of catheter 30 at its distal end. Using the conventional method and equipment of FIG. 1B, two hands are again required to advance the distal end of the catheter in a soft manner: the surgeon uses one hand to secure stylet 20 in a stationary position, while catheter 30 is manually advanced by forceps 19 held in the surgeon's other hand. The conventional two-handed soft pass technique is inefficient and cumbersome. In particular, when ventricular catheter placement is being performed as part of a ventricular shunt operation in conjunction with equipment such as the Caroline Guide (see, for example, U.S. Pat. No 5,569,267 to Howard, III et al.) the two-handed soft pass technique of the prior art requires a surgical assistant to provide an "extra hand."

FIG. 2A shows a catheter advancing piece or cylinder 10 according to one embodiment of the instant invention. Catheter advancing piece 10 includes a rod 12 having a distal end 12a and a proximal end 12b. Rod 12 has a bore 14 therethrough, i.e. bore 14 extends the entire length of rod 12. According to a preferred embodiment, rod 12 may be cylindrical or substantially cylindrical in shape. A grasping unit 16 is fixedly attached or affixed to rod 12, and serves as a convenient means for holding and manipulating rod 12 and catheter advancing piece 10. According to a preferred embodiment, grasping unit 16 includes first and second finger pieces (FIG. 3A).

Figure 2B:
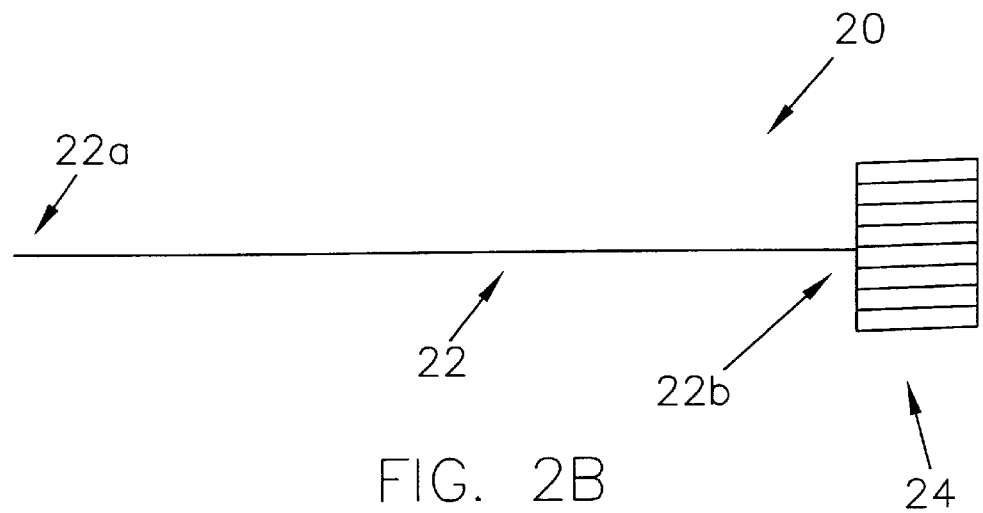
FIG. 2B shows a stylet having a holding unit, according to one embodiment of the invention.
Figure 4A:
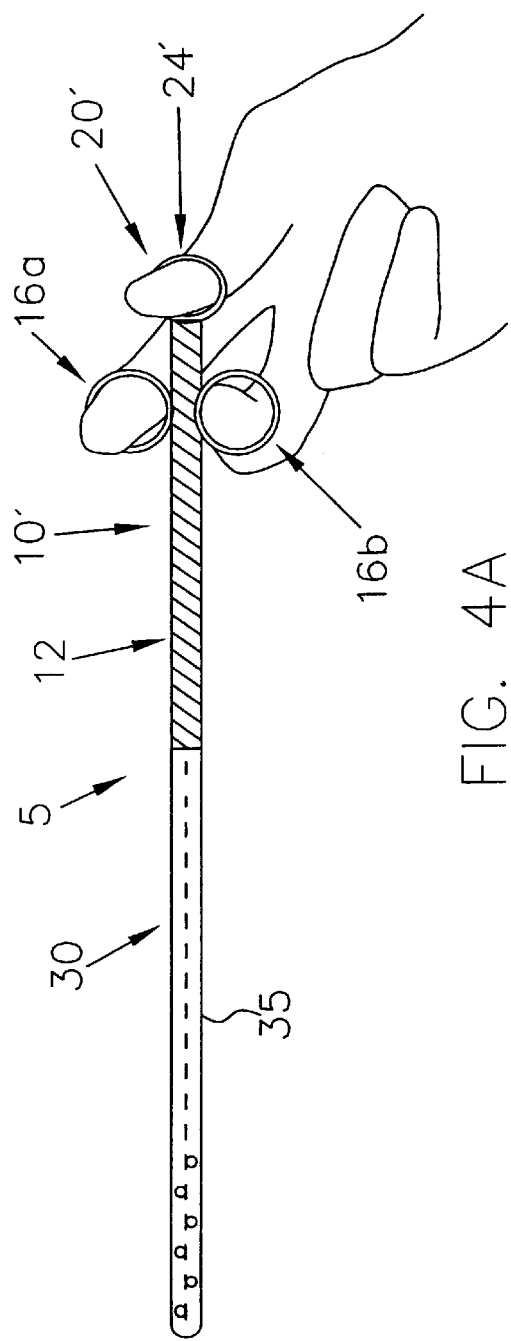
FIG. 4A shows a catheter advancing assembly in the assembled state, and depicted as being held by a thumb, an index finger, and a middle finger, with the catheter advancing assembly in the unextended position.

FIG. 2B shows a stylet 20 according to one embodiment of the instant invention, stylet 20 including a shaft 22 having a distal end 22a and a proximal end 22b. Shaft 22 is essentially a narrow cylinder having a length greater than the length of rod 12, and a diameter substantially the same as, or slightly less than, the diameter of bore 14 in rod 12. Bore 14 is capable of accommodating a portion of shaft 22 when shaft 22 is coupled to catheter advancing piece 10. For example, with the catheter advancing assembly 5 in the assembled state, bore 14 houses the proximal end of shaft 22 when catheter advancing assembly 5 is in the unextended position (FIG. 4A).

Figure 2C:
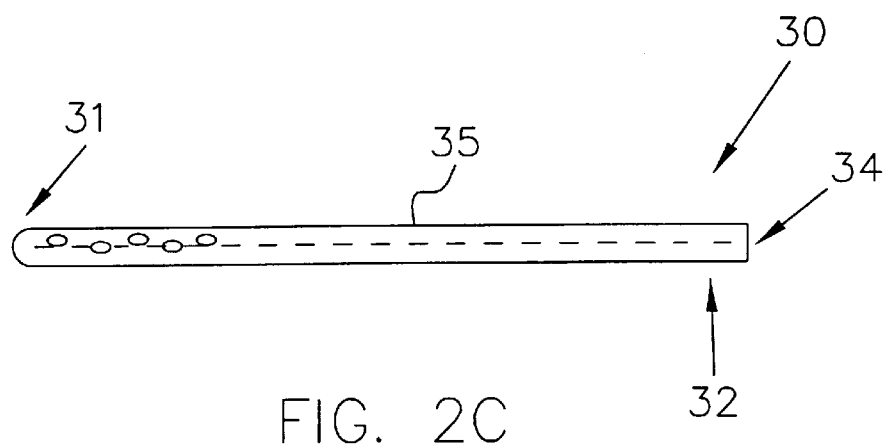
FIG. 2C shows a ventricular catheter for engagement with the stylet of FIG. 2B, according to another embodiment of the invention.

According to a preferred embodiment shaft 22 may be formed from a length of rigid wire, or the like, such that it can move freely in a longitudinal direction within bore 14. A holding unit 24 is affixed at proximal end 22b of shaft 22. Holding unit 24 provides a convenient means for holding and manipulating stylet 20. According to a preferred embodiment, holding unit 24 is in the form of a thumb piece (FIG. 3B). FIG. 2C shows a ventricular catheter 30 including a channel 34 therein for coupling or engagement with shaft 22 of FIG. 2B. Catheter 30 includes a distal end 31 having a plurality of drainage holes 35 therein, and a proximal end 32. Channel 34 which extends along the longitudinal axis of catheter 30, is capable of housing a portion of shaft 22 and allows shaft 22 to move freely in a longitudinal direction within channel 34. Preferably the width or diameter of rod 12 is the same or substantially the same as the diameter of proximal end 32 of catheter 30.

Figure 3A:
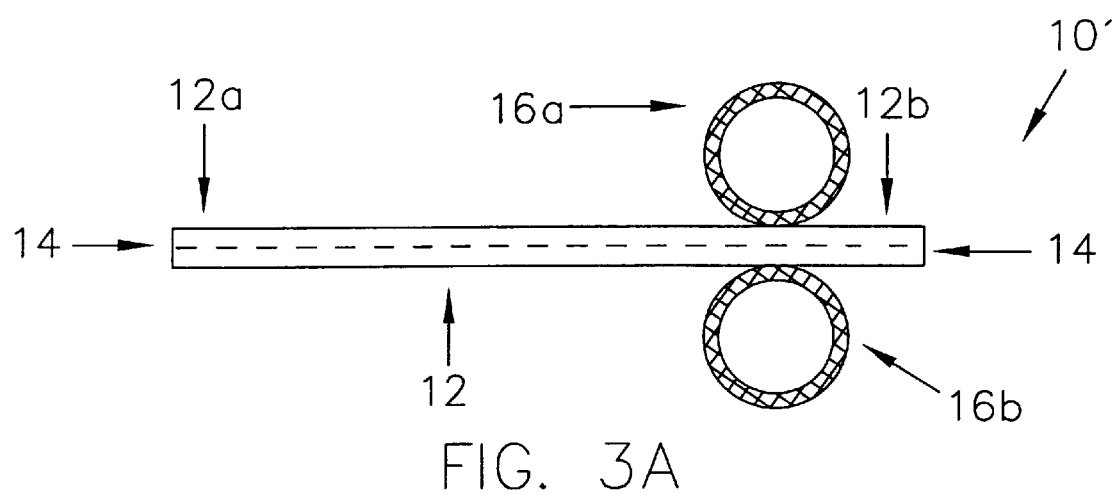
FIG. 3A is shows a catheter advancing piece having first and second finger pieces, according to another embodiment of the invention.
Figure 3B:
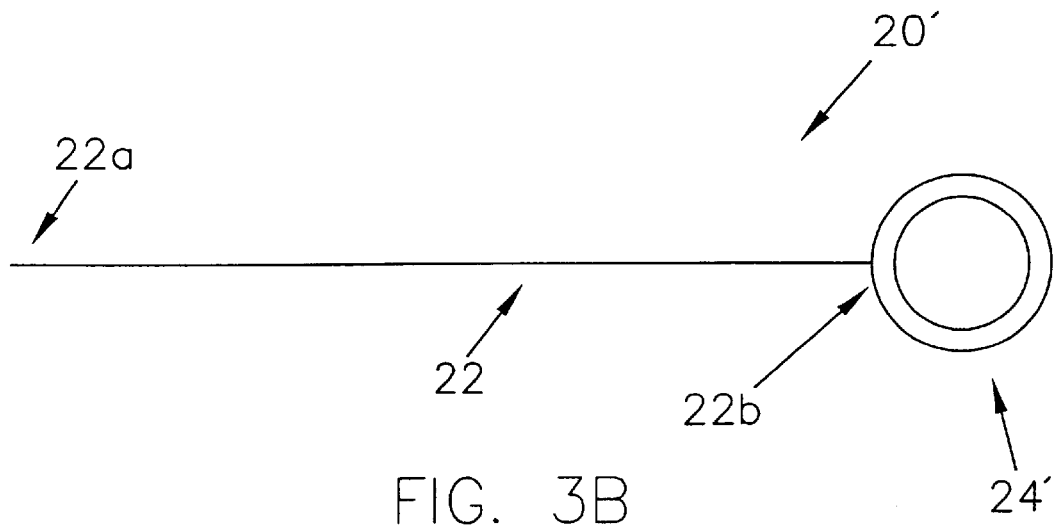
FIG. 3B shows a stylet having a thumb piece, according to another embodiment of the invention.

FIG. 3A shows a catheter advancing piece or cylinder 10', according to a currently preferred embodiment of the invention. Catheter advancing piece 10' includes a rod 12 having a distal end 12a and a proximal end 12b. Rod 12 has a bore 14 therethrough, i.e. bore 14 extends the entire length of rod 12. Preferably, rod 12 is substantially cylindrical in shape and has a diameter the same, or substantially the same, as the diameter of proximal end 32 of catheter 30. In the assembled state of catheter advancing assembly 5 (FIGS. 4A, 4B) distal end 12a of rod 12 abuts against the proximal end 32 of catheter 30, and during use of catheter advancing assembly 5 distal end 12a of rod 12 pushes against proximal end 32 to advance catheter 30.

A first finger piece 16a and a second finger piece 16b are affixed bilaterally to rod 12. First finger piece 16a and second finger piece 16b may each be in the form of a ring of metal, plastic, or similar solid material, and are designed to accommodate at least one finger, preferably at least two fingers such as the index finger and the middle finger, respectively, of the surgeon or user of catheter advancing piece 10'. Thus, first finger piece 16a and second finger piece 16b serve as a convenient means for holding and manipulating rod 12 and catheter advancing piece 10'. According to a currently preferred embodiment, the first finger piece and the second finger piece are affixed bilaterally to the rod at a distance ranging from about 0 to about 4 cm. from proximal end 12b of rod 12.

Figure 4B:
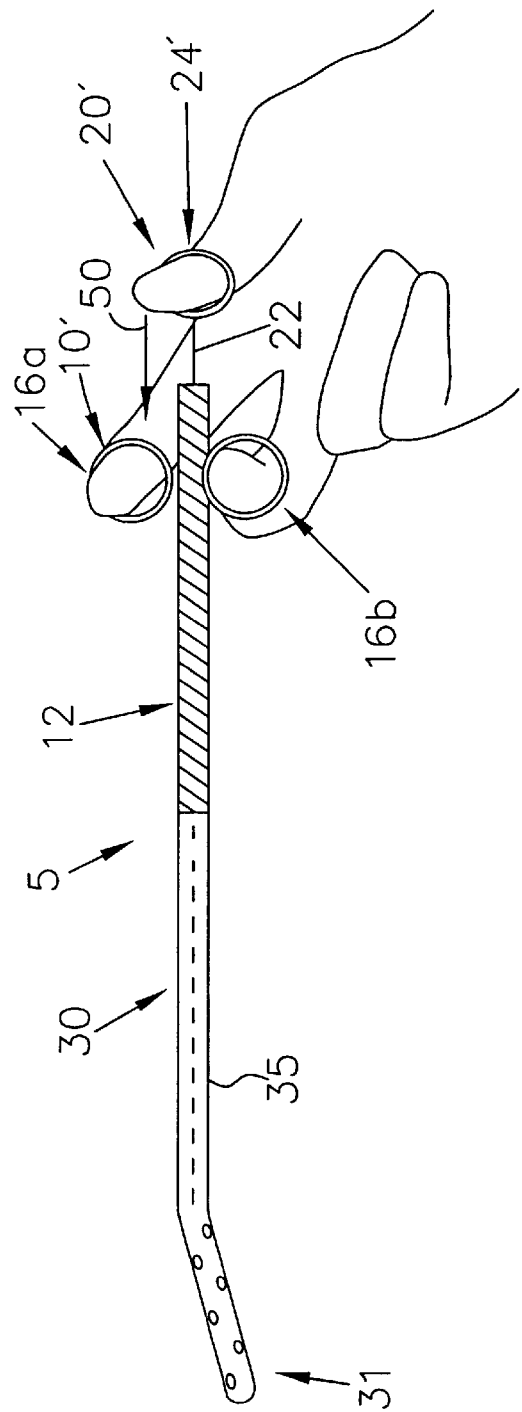
FIG. 4B shows a catheter advancing assembly in the assembled state, depicted as being held by a thumb, an index finger, and a middle finger, with the catheter advancing assembly in the extended position, according to one embodiment of the invention.

FIG. 3B shows a stylet 20' according to one embodiment of the invention. Stylet 20' includes a shaft 22 having a distal end 22a and a proximal end 22b. Shaft 22 is essentially a narrow cylinder having a length greater than the length of rod 12, and a diameter substantially the same as, or slightly less than, the diameter of bore 14 in rod 12, such that shaft 22 can move freely in a longitudinal direction within bore 14 when shaft 22 is coupled to catheter advancing piece 10' (FIGS. 4A, 4B). Stylet 20' further includes a thumb piece 24' affixed at proximal end 22b of shaft 22. Preferably, thumb piece 24' is in the form of a ring of metal, plastic, or other fairly rigid material, and is designed to have dimensions suitable to accommodate a thumb of the surgeon or user of stylet 20'.

Figure 3C:
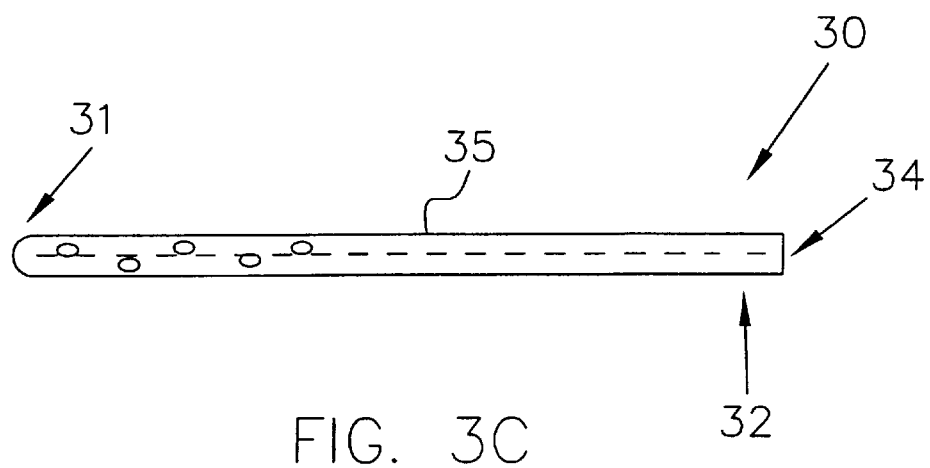
FIG. 3C shows a ventricular catheter for engagement with the stylet of FIG. 3B, according to another embodiment of the invention.

FIG. 3C shows a ventricular catheter 30 for coupling or engagement with stylet 20' of FIG. 3B. Catheter 30 includes a distal end 31 having a plurality of drainage holes 35 therein and a proximal end 32. Catheter 30 has a channel 34 therein, the channel extending along the longitudinal axis of catheter 30 and housing a portion of shaft 22 when stylet 20' is coupled to catheter 30. Channel 34 allows shaft 22 to move freely in a longitudinal direction therein.

FIG. 4A shows a catheter advancing assembly 5 in the assembled state, including stylet 20' coupled to catheter advancing piece 10' and catheter 30. Catheter advancing assembly 5 is depicted in FIG. 4A as being held by a thumb, an index finger, and a middle finger, in particular thumb piece 24' is held by a thumb, while first and second finger pieces 16a and 16b are grasped by an index finger and a middle finger, respectively. Catheter advancing assembly 5 is shown in FIG. 4A as being in the unextended position. In this position, proximal end 22b of shaft 22 is fully housed, or substantially fully housed, within catheter advancing piece 10'; while distal end 31 of catheter 30 is occupied or substantially occupied by distal end 22a of shaft 22; and at the same time, proximal end 12b of rod 12 is in contact with, or lies in close proximity to, thumb piece 24'. In contrast, when catheter advancing assembly 5 is in the extended position (FIG. 4B) proximal end 22b of shaft 22 is exposed as proximal end 12b of rod 12 moves away from thumb piece 24', while distal end 31 of catheter 30 is advanced beyond distal end 22a of shaft 22.

FIG. 4B shows catheter advancing assembly 5 in the assembled state as being held by a thumb, an index finger, and a middle finger, as described above with reference to FIG. 4A, but with assembly 5 in the extended position. By extending the index and middle fingers in the direction indicated by the arrow marked 50, while the thumb is held stationary, catheter advancing piece 10' is advanced relative to shaft 22 of stylet 20'. In this manner, catheter advancing piece 10' serves to advance catheter 30 along a stationary stylet shaft 22. As a result, when catheter advancing assembly 5 is moved to the extended position as depicted in FIG. 4B, distal end 31 of catheter 30 is advanced in a soft manner, i.e. without shaft 22 therein.

Figure 5A:
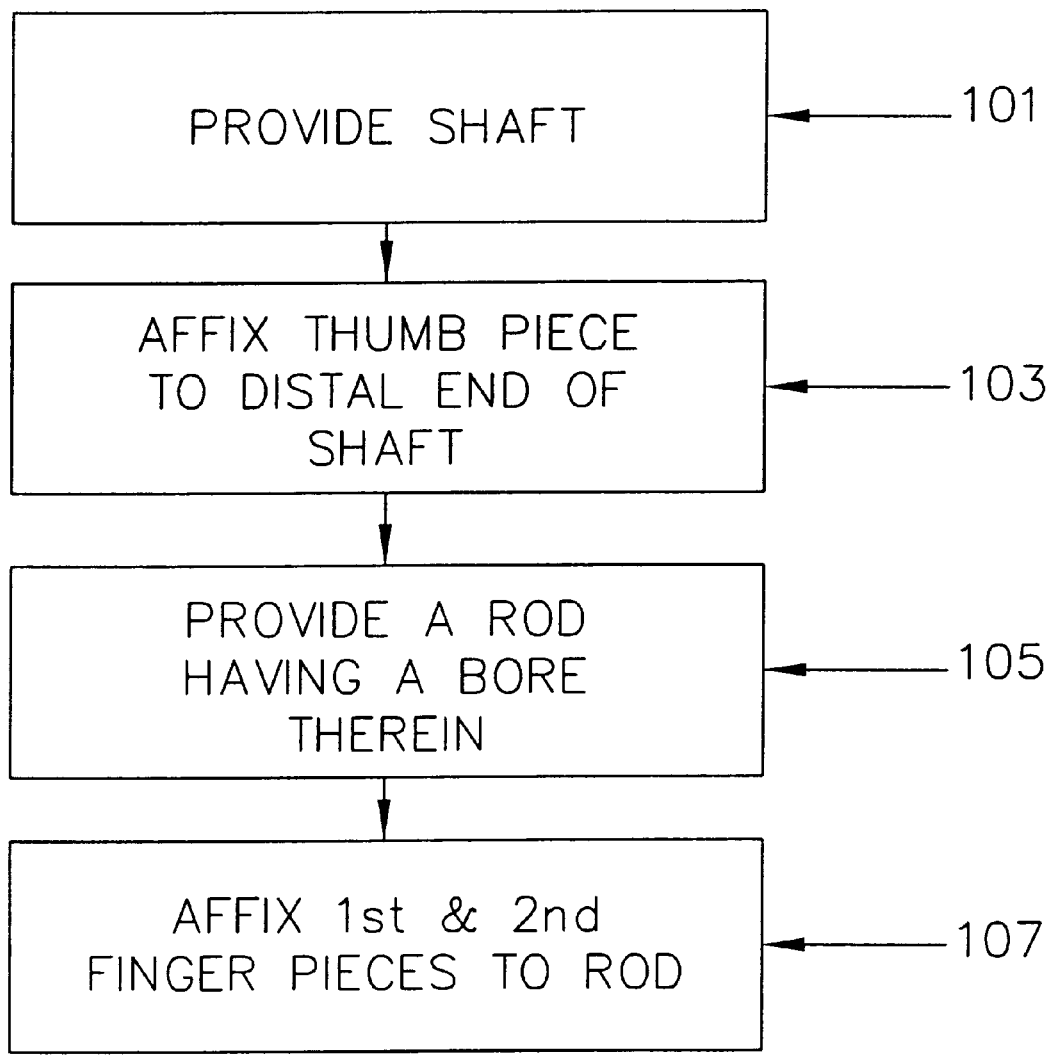
FIG. 5A summarizes the steps involved in a method for making a catheter advancing assembly, according to another embodiment of the invention.

FIG. 5A summarizes the steps involved in a method for making a catheter advancing assembly, according to another embodiment of the invention, in which step 101 involves providing a shaft of a stylet. The shaft may be in the form of a length of fairly rigid wire of suitable length. Step 103 involves affixing a thumb piece to the distal end of the shaft. The thumb piece may be in the form of a metal ring or similar structure suitable for accommodating a thumb of a person operating the catheter advancing assembly. Step 105 then involves providing a rod of a catheter advancing cylinder. The rod has a length less than the length of the shaft, and has a bore running throughout the entire length of the rod. The bore is substantially cylindrical in shape and is capable of housing a portion of the shaft. The diameter of the bore is the same as, or slightly less than, the diameter of the stylet shaft such that the shaft can move freely within the bore in a longitudinal direction. Step 107 involves affixing or fixedly attaching a first finger piece and a second finger piece to the rod. Preferably each of the first and second finger pieces is in the form of a ring of metal, plastic, or other rigid material, of suitable dimensions to accommodate an index finger or a middle finger of a person operating the catheter advancing assembly. According to a currently preferred embodiment, the first finger piece and the second finger piece are affixed bilaterally to the rod towards the proximal end of the rod. Preferably the first finger piece and the second finger piece are affixed bilaterally to the rod at a distance ranging from about 0 to about 4 cm, from the proximal end of the rod. The rod may be coupled to the stylet by inserting the distal end of the shaft through the bore in the proximal end of the rod and sliding the rod towards the proximal end of the shaft. Thereafter, a ventricular catheter may be coupled to the stylet by inserting the distal end of the shaft into the channel at the proximal end of the catheter, and moving the proximal end of the catheter towards the distal end of the rod.

Figure 5B:
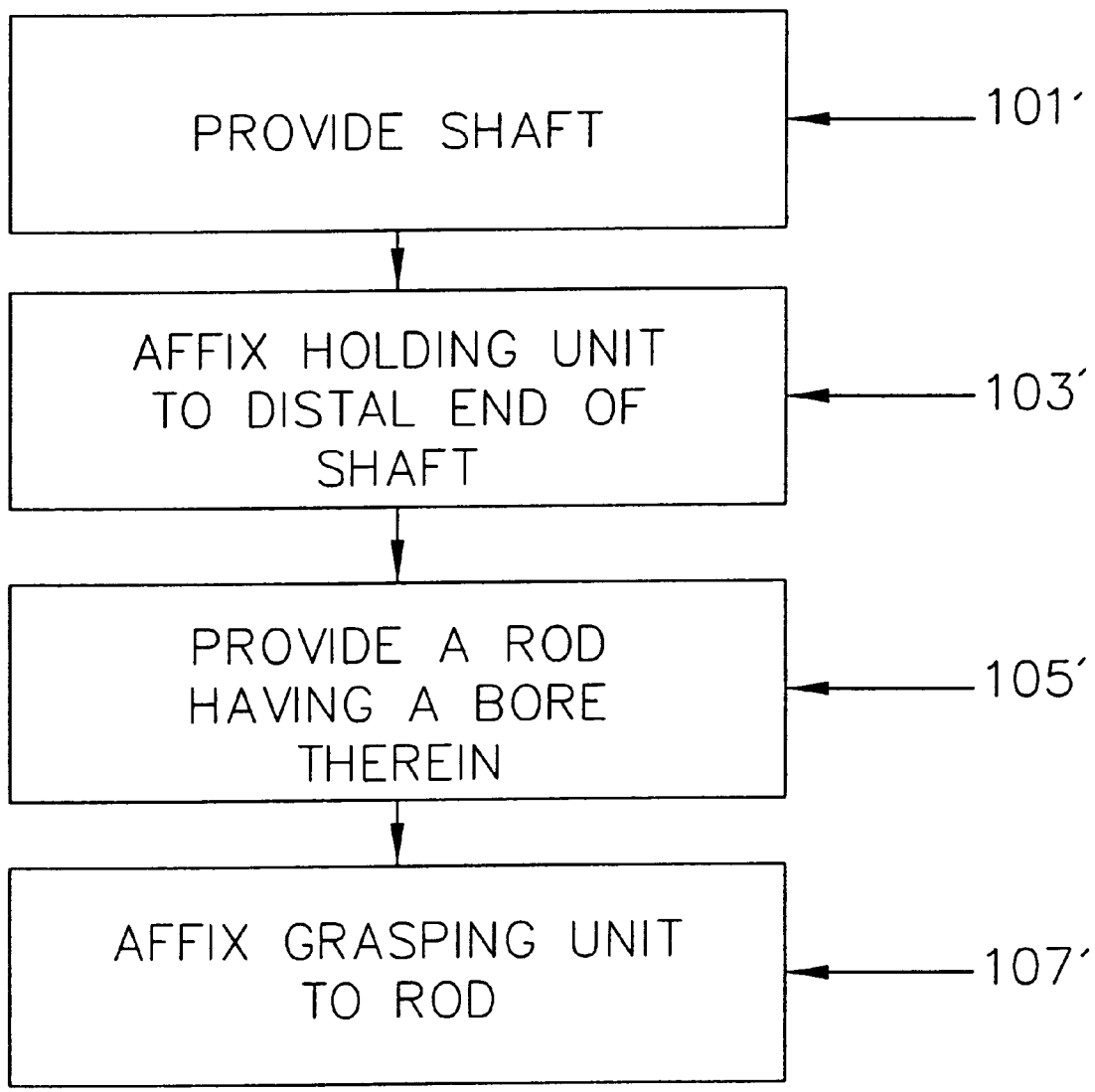
FIG. 5B summarizes the steps involved in a method for making a catheter advancing assembly, according to another embodiment of the invention.

FIG. 5B summarizes the steps involved in a method for making a catheter advancing assembly, according to another embodiment of the invention, in which step 101' involves providing a shaft of a stylet. The shaft may be in the form of a length of fairly rigid wire of suitable length. Step 103' involves affixing a holding unit to the distal end of the shaft. The holding unit may take the form of any suitable structure allowing the holding and manipulation of the stylet. Step 105' then involves providing a rod of a catheter advancing piece. The rod has a bore running throughout the entire length of the rod. The bore is substantially cylindrical in shape and is capable of housing at least a portion of the shaft. The diameter of the bore is the same as, or slightly less than, the diameter of the stylet shaft such that the shaft can move freely within the bore in a longitudinal direction. Step 107' involves affixing or fixedly attaching a grasping unit to the rod. According to a preferred embodiment, the grasping unit may be in the form of a pair of bilaterally juxtaposed rings of a substantially rigid material, and having suitable dimensions to accommodate an index finger or a middle finger of a person operating the catheter advancing assembly. The grasping unit and holding units may independently be detachable and/or disposable in this and other embodiments of the invention. The grasping unit and holding units may also be provided in a variety of sizes to fit the hand, preferably the one or more fingers and thumb of the surgeon.

Figure 6:
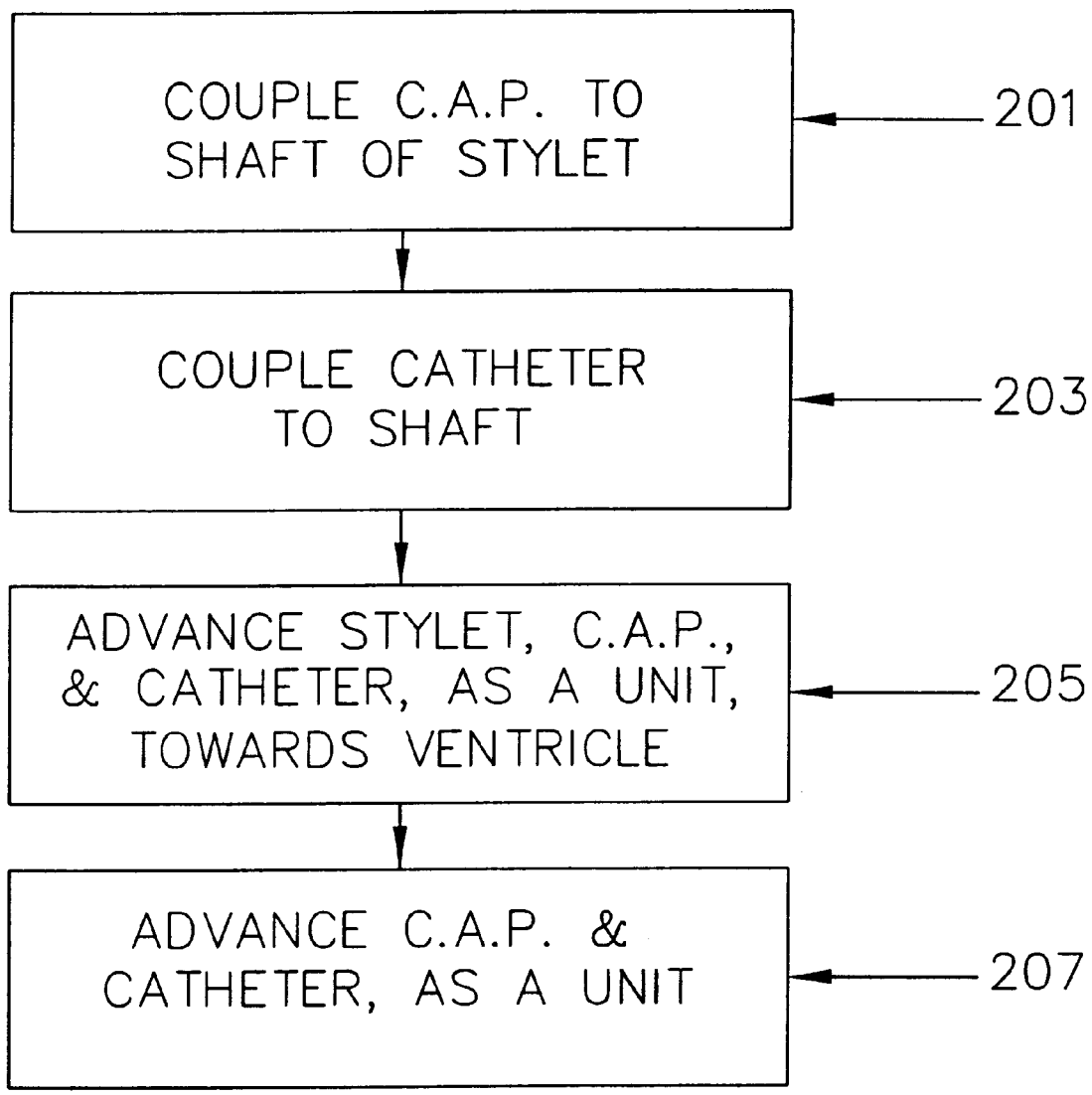
FIG. 6 summarizes a series of steps involved in a method for soft passing a ventricular catheter within a cerebral ventricle of a patient, according to another embodiment of the invention.

FIG. 6 summarizes a series of steps involved in a method for soft passing a ventricular catheter within a cerebral ventricle of a patient, according to another embodiment of the invention. Thus, step 201 involves coupling a catheter advancing piece to the shaft of a stylet, such that the proximal end of the shaft is housed within a bore of the catheter advancing piece. Step 203 then involves coupling a ventricular catheter having a channel therein to the distal end of the shaft, such that the distal end of the shaft is housed within the channel. Step 205 involves advancing the stylet, the catheter advancing piece, and the ventricular catheter, as a unit, towards a cerebral ventricle until the distal end of the ventricular catheter has penetrated the cerebral ventricle. Prior to step 205, a burr hole must be formed at a suitable location in the patient's skull for introduction of the catheter therethrough. A preferred location for a burr hole is the parieto-occipital region (see, for example, U.S. Pat. No. 5,569,267 to Howard, III et al., and references cited therein). Step 207 involves advancing the ventricular catheter and the catheter advancing piece, as a unit, by advancing at least one, preferably two, finger pieces of the catheter advancing piece while the stylet is held in a stationary position by means of the thumb piece. The finger pieces may be so advanced, for example, by extending the index and middle fingers while the thumb is held stationary. In this manner the ventricular catheter is advanced along the stationary shaft of the stylet such that the distal end of the catheter is soft passed within the cerebral ventricle.

The catheter advancing single-handed soft passer of the invention is useful, for example, for the placement of a catheter into a cerebral ventricle of a patient.

Although the catheter advancing assembly of the instant invention has been described herein primarily with respect to advancing a ventricular catheter within a cerebral ventricle, apparatus and methods of the instant invention may find other applications for advancing a catheter in other parts of the body. The apparatus and methods of the instant invention may additionally find applications in veterinary medicine.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A catheter advancing assembly for single-handed soft passing a ventricular catheter, comprising:
   a stylet having a shaft and a holding unit;
   a catheter advancing piece including a rod and a grasping unit, said rod having a longitudinal bore therethrough capable of housing at least a portion of said shaft, and said shaft capable of moving longitudinally within said bore; and a catheter having a channel therein capable of housing at least a portion of said shaft, wherein an end of said shaft does not extend beyond an end of said catheter, wherein said catheter advancing piece is configured to be capable of advancing said catheter, wherein a diameter of the rod and a diameter of the catheter are substantially equal, and wherein the catheter is a ventricular catheter having a plurality of drainage holes, and wherein the shaft is rigid.

2. The catheter advancing assembly of claim 1, wherein the shaft is essentially rigid and includes a distal end and a proximal end, wherein the shaft has a diameter substantially the same as the diameter of the bore, and wherein the holding unit is affixed to the shaft, substantially near the proximal end of the shaft.

3. The catheter advancing assembly of claim 2, wherein the holding unit comprises a thumb piece.

4. The catheter advancing assembly of claim 3, wherein the thumb piece comprises a ring.

5. The catheter advancing assembly of claim 1, wherein the grasping unit comprises a first finger piece and a second finger piece arranged bilaterally on the rod.

6. The catheter advancing assembly of claim 5, wherein the rod has a distal end and a proximal end, wherein the first finger piece and the second finger piece are arranged substantially at the proximal end of the rod.

7. The catheter advancing assembly of claim 1, wherein the shaft has a length greater than the bore.

8. The catheter advancing assembly of claim 6, wherein the holding unit comprises a ring and the first and second finger pieces each comprise a ring, and wherein the holding unit and first and second finger pieces are arranged such that holding unit and the first and second finger pieces can be simultaneously grasped by one hand.

9. The catheter advancing assembly of claim 8, wherein the first and second finger pieces are adapted to receive a first and second finger on a hand of a user and the holding unit is adapted to receive a thumb on the same hand.

10. The catheter advancing assembly of claim 1, wherein the catheter is rigid when the portion of the shaft is housed within the channel.

11. A catheter advancing assembly for single-handed soft passing a ventricular catheter, comprising:

a ventricular catheter having a proximal end and a distal end and a longitudinal channel;

a catheter advancing piece having a grasping unit and a longitudinal bore; and a stylet having a holding unit and a shaft conformed to fit within the longitudinal channel of the ventricular catheter and the longitudinal bore of the catheter advancing piece, wherein a length of the shaft is greater than the length of the longitudinal bore and less than a combined length of the longitudinal bore plus the longitudinal channel, and wherein the catheter advancing piece is configured to advance the ventricular catheter.

12. The catheter advancing assembly of claim 11, wherein the grasping unit comprises two rings, forming a first finger piece and a second finger piece.

13. The catheter advancing assembly of claim 12, wherein the first and second finger pieces are arranged bilaterally on the catheter advancing piece.

14. The catheter advancing assembly of claim 11, wherein the holding unit and the grasping unit are arranged such that they can be simultaneously grasped with one hand.

15. The catheter advancing assembly of claim 11, wherein the ventricular catheter has a plurality of holes therein.

16. A method for single-handed soft passing a ventricular catheter within a cerebral ventricle of a patient, comprising:

a) coupling a catheter advancing piece to a shaft of a stylet, the shaft having a proximal end and a distal end, wherein the proximal end of the shaft is housed within a bore of the catheter advancing piece and wherein the shaft is rigid;

b) coupling a ventricular catheter to the distal end of the shaft, the ventricular catheter having a channel therein and a plurality of drainage holes, wherein the distal end of the shaft is housed within the channel;

c) advancing the ventricular catheter, the catheter advancing piece, and the stylet, as a unit, towards a cerebral ventricle until the distal end of the ventricular catheter has penetrated the cerebral ventricle; and d) while the stylet is held in a stationary position, advancing the ventricular catheter and the catheter advancing piece, as a unit, wherein a diameter of the catheter advancing piece and a diameter of the ventricular catheter are substantially equal.

17. The method of claim 16, further comprising the step of forming a burr hole through which the ventricular catheter may be advanced towards the cerebral ventricle.

18. The method of claim 16, wherein said step a) comprises coupling a catheter advancing piece to a shaft of a stylet, wherein the catheter advancing piece includes at least one finger piece and wherein the stylet includes a thumb piece.

19. The method of claim 18, further comprising the steps of holding the thumb piece by a thumb, and grasping the at least one finger piece and a second finger piece by an index finger and a middle finger, respectively.

20. The method of claim 19, wherein step d) comprises extending the index finger and the middle finger while holding the thumb piece stationary.

21. The method of claim 16, wherein step d) comprises advancing the distal end of the ventricular catheter within the cerebral ventricle in a soft manner.

\* \* \* \* \*